US006228883B1

(12) United States Patent
Riggs

(10) Patent No.: US 6,228,883 B1
(45) **Date of Patent: *May 8, 2001**

(54) SEED TREATMENT FUNGICIDES FOR CONTROL OF PLANT DISEASES

(75) Inventor: Jennifer Lynn Riggs, Plano, TX (US)

(73) Assignee: Gustafson, Inc., Plano, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/132,927

(22) Filed: Aug. 12, 1998

Related U.S. Application Data

(60) Provisional application No. 60/059,293, filed on Sep. 18, 1997.

(51) Int. Cl.$^7$ .......................... A01N 37/34; A01N 47/10

(52) U.S. Cl. .......................... 514/479; 514/478; 514/491; 514/528

(58) Field of Search .......................... 514/528, 491, 514/478, 479

(56) References Cited

U.S. PATENT DOCUMENTS

| | | | |
|---|---|---|---|
| 3,379,610 | 4/1968 | Channing et al. | 167/32 |
| 3,905,995 | 9/1975 | Enoki et al. | 260/309 |
| 3,957,847 | 5/1976 | Davidson | 260/465.4 |
| 4,742,079 | 5/1988 | Devoise-Lambert et al. | 514/528 |
| 5,007,953 | 4/1991 | Chollett | 71/77 |
| 5,776,976 | 7/1998 | Dehne et al. | 514/479 |

FOREIGN PATENT DOCUMENTS 1470740 4/1977 (GB) .

OTHER PUBLICATIONS

Tomlin, The Pesticide Manual Incorporating the Agrochemicals Handbook, 10$^{th}$ Ed. (1995) pp. 257, 258, 987 & 988.*

Samoucha et al, "Systemicity and persistence of cymoxanil in mixture with oxadixyl and mancozeb against *Phytophthora infestans* and *Plasmopara viticola*", Crop Protection 6(6):393–398 (Dec. 1987).

Cohen et al, "Uptake, translocation and degradation of [$^{14}$C]cymoxanil in tomato plants", Crop Protection 12(4):284–292 (Jun. 1993).

"Glasshouse Evaluation of Fungicides For The Control Of Sunflower Downy Mildew Plasmopara–Halstedii", Oros G. and Viranyi, F., Biological Abstract, vol. 84, Abstract No. 8605, Annals of Applied Biology, 110(1), 1987, pp. 53–64;

"Field Control Of Potato Late Blight By Synergistic Fungicidal Mixtures", Samoucha, Yair and Cohen, Yigal, Chemical Abstract, vol. 111, No. 25, Dec. 18, 1989, Plant Dis. 73(9), 1989, pp. 751–753.

"Efficay Over Time Of Cymoxanil Mixtures In Controlling Late Blight In Potatoes Incited By A Phenylamide–Resistant Isolate Of Phytophthora Infestans", Samoucha, Y, Levy, R.S., Cohen, Y., Chemical Abstract, vol. 109, No. 13, Sep. 26, 1988, pp. 210–215.

"Synergistic Interactions Of Cymoxanil Mixtures In The Control of Metalaxyl–Resistant Phytophthora Infestans Of Potato", Samoucha, Yair and Cohen, Yigal, Chemical Abstract, vol. 109, No. 15, Oct. 10, 1988, Phytopathology, 78(6), 1988, pp. 636–640.

"Compositions For Fighting Tuber And Bulb Rot–Containing Mancozeb Combined With Benomil, Methyl Thiophanate Or Thia–Bendazole And Tetracycline Or Chlor–amphenicol", Alexandri, A., Baicu, T., Bftlan, E., and Plamadeala, B., Database WPI, Derwent Publications, Ltd., London, GB, AN 83–762767&RO–A–80510.

* cited by examiner

*Primary Examiner*—Allen J. Robinson
(74) *Attorney, Agent, or Firm*—Sidley & Austin

(57) ABSTRACT

A method for combatting plant fungi in a plant, which comprises applying to the seeds or tubers of the plant, an effective amount of a fungicidal composition comprising a fungicidally effective amount of a 2-alkoxyiminoacetamide compound, optionally in admixture with one or both of an alkylene bis-dithiocarbamate complex salt and a thiophanate compound. Fungicidal compositions comprising a fungicidally effective amount of a 2-alkoxyiminoacetamide compound, an alkylene bis-dithiocarbamate complex salt, and a thiophanate compound, are also described.

22 Claims, No Drawings

SEED TREATMENT FUNGICIDES FOR CONTROL OF PLANT DISEASES

Reference is made to and priority claimed from U.S. Provisional Application Serial No. 60/059,293, filed Sep. 18, 1997, entitled "SEED TREATMENT FUNGICIDES FOR CONTROL OF PLANT DISEASES."

FIELD OF THE INVENTION

This invention relates to a method for controlling fungus diseases in plants by applying to the seed or tuber a fungicidally effective amount of a 2-alkoxyiminoacetamide compound such as cymoxanil, optionally in admixture with one or more of an alkylene bis-dithiocarbamate complex salt such as mancozeb, and a thiophanate compound such as thiophanate-methyl. This invention also relates to a fungicidal composition comprising, in a fungicidally effective aggregate amount, a 2-alkoxyiminoacetamide compound, an alkylene bis-dithiocarbamate complex salt, and a thiophanate compound.

BACKGROUND OF THE INVENTION

Late Blight is the devastating disease that affected the Irish potato crop over 150 years ago Today, however, the Late Blight fungus, *Phytophthora infestans*, is much different than its ancestors. New strains of *P. infestans* have evolved that are fungicide resistant and which are more aggressive with respect to pathogenicity on the potato tuber. As a result, the disease can now be introduced into potato fields by means of infected seed tubers more efficiently than in the past.

It is the purpose of this invention to provide a novel method for combatting plant fungi, particularly phytopathogenic fungi such as *Phytophthora infestans*. It is a purpose to provide a novel fungicidal composition useful for combatting plant fungi, particularly phytophogenic fungi such as *Phytophthora infestans*.

SUMMARY OF THE INVENTION

This invention relates to a method for combatting plant fungi in a plant, which comprises applying to the seeds or tubers of the plant, a fungicidally effective amount of:

a) a 2-alkoxyiminoacetamide compound of the formula:

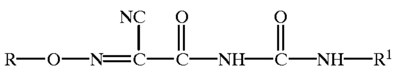

wherein R is methyl or ethyl and $R^1$ hydrogen, $C_1$–$C_4$ alkyl or allyl, preferably, $C_1$–$C_4$ alkyl, more preferably, methyl or ethyl; or b) the 2-alkoxyiminoacetamide compound in admixture with one or more compounds selected from the group consisting of:

i) an alkylene bis-dithiocarbamate complex salt of the formula:

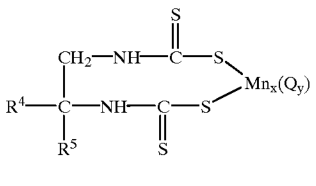

wherein $R^4$ and $R^5$ are each, independently, hydrogen or $C_1$–$C_6$ alkyl, preferably, hydrogen or $C_1$–$C_4$ alkyl, more preferably, hydrogen, methyl or ethyl; Q is Zn, Fe, or Cu, preferably, Zn; and the ratio of x to y is from about 3:1 to about 100:1, preferably, about 5:1 to about 20:1, more preferably, about 6:1 to about 10:1.

and ii) a thiophanate compound of the formula:

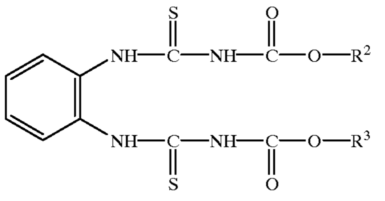

wherein $R^2$ and $R^3$ are each, independently, $C_1$–$C_6$ alkyl, preferably, $C_1$–$C_4$ alkyl, more preferably, methyl or ethyl.

This invention further relates to a fungicidal composition comprising:

a) a 2-alkoxyiminoacetamide compound of the formula:

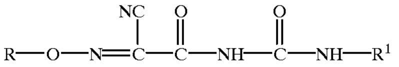

wherein R is methyl or ethyl and $R^1$ hydrogen, $C_1$–$C_4$ alkyl or allyl, preferably, $C_1$–$C_4$ alkyl, more preferably, methyl or ethyl;

b) an alkylene bis-dithiocarbamate complex salt of the formula:

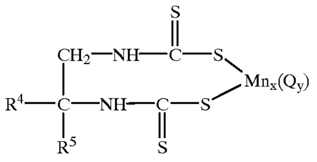

wherein $R^4$ and $R^5$ are each, independently, hydrogen or $C_1$–$C_6$ alkyl, preferably, hydrogen or $C_1$–$C_4$ alkyl, more preferably, hydrogen, methyl or ethyl; Q is Zn, Fe, or Cu, preferably, Zn; and the ratio of x to y is from about 3:1 to about 100:1, preferably, about 5:1 to about 20:1, more preferably, about 6:1 to about 10:1; and c) a thiophanate compound of the formula:

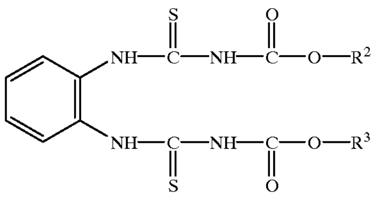

wherein $R^2$ and $R^3$ are each, independently, $C_1$–$C_6$ alkyl, preferably, $C_1$–$C_4$ alkyl, more preferably, methyl or ethyl, in an effective aggregate amount.

DESCRIPTION OF THE INVENTION

The 2-alkoxyiminoacetamide compounds, alkylene bis-dithiocarbamate complex salts, and thiophanate compounds useful in the method and composition of this invention, are known in the art, as are methods for their preparation. See, e.g., U.S. Pat. Nos. 3,957,847; 3,379,610; and 5,571,443, respectively.

The method and composition of this invention are particularly suitable for use against *Phytophthora infestans* on or in potato plants and tubers.

The composition of this invention and the compounds useful in the method of this invention can be formulated in conventional ways. Examples of useful formulations include slurries, solid seed coatings, soaks, dusts on the surface of the seed or tuber, solutions, suspensions, emulsions, wettable powders, emulsifiable concentrates, and the like. The formulations, in general, comprise about 1% to 99% by weight of active ingredient. The formulations can additionally comprise additional additives such as surfactants, solid or liquid diluents, pigments, thickeners, and the like. The method of application of the formulations to the seeds or tubers can vary depending, e.g., on the compounds and/or the formulation used.

In general, the seed or tuber should be treated with about 50 to about 1200 ppm, preferably between about 300 to about 900 ppm, most preferably, about 700 ppm, per 100 pounds ("cwt") of seed or tuber, of the composition of this invention or of the compounds useful in the method of this invention.

This invention preferably relates to a method for combatting plant fungi in a plant, which comprises applying to the seeds or tubers of the plant, an effective amount of a fungicidal composition comprising a fungicidally effective amount of:

a) cymoxanil; or b) cymoxanil in admixture with one or more of the group consisting of mancozeb and thiophanate-methyl.

This invention further preferably relates to a fungicidal composition comprising cymoxanil, mancozeb and thiophanate-methyl, in an effective aggregate amount.

Cymoxanil, mancozeb and thiophanate-methyl are all known compounds.

Cymoxanil (a foliar fungicide sold under the trademarks CURZATE and DPX-3217) is 2-cyano-N-[(ethylamino) carbonyl]-2-(methoxyimino)-acetamide.

Mancozeb (a fungicide sold under the trademarks MANZATE-200 and DITHANE M-45) is a mixture of [[1,2-ethanediylbis-(carbamodithioato)](2-)]manganese and [[1,2-ethanediylbis(carbamothioato)](2)-]zinc.

Thiophanate-methyl (a systemic fungicide sold under the trademarks TOPSIN M and NF-44) is dimethyl[1,2-phenylene-bis-(iminocarbono-thioyl)-bis-[carbamate].

In the method of this invention wherein cymoxanil is admixed with thiophanate-methyl, in general, satisfactory results can be obtained when the weight ratio of cymoxanil:thiophanate-methyl is from about 1:3 to 3:1, preferably 1:2 to 2:1, and more preferably, 1:1.5 to 1.5.1.

In the method of this invention wherein cymoxanil is admixed with mancozeb, in general, satisfactory results can be obtained when the weight ratio of cymoxanil:mancozeb is from about 1:16 to 3:1, preferably 1:8 to 2:1, and more preferably, 1:3 to 1.5:1.

In the method of this invention wherein cymoxanil, mancozeb and thiophanate-methyl are admixed, in general, satisfactory results can be obtained when the weight ratio of cymoxanil:mancozeb:thiophanate-methyl is from about 3:1:1 to about 1:16:6, preferably, about 1.5:1:1 to about 1:8:3.

Similarly, in the composition of this, invention, in general, satisfactory results can be obtained when the weight ratio of cymoxanil:mancozeb:thiophanate-methyl is from about 3:1:1 to about 1:16:6, preferably, about 1.5:1:1 to about 1:8:3.

The formulations can comprise from 0 to about 20% of an agriculturally acceptable surfactant such as wetting and dispersing agents, e.g., the condensation product of formaldehyde with naphthalene sulphonate, an alkylarylsulphonate, a lignin sulphonate, a fatty sulphate, an ethoxylated alkylphenol and an ethoxylated fatty alcohol. The formulations can additionally comprise from about 10 to about 99% of an agriculturally acceptable solid or liquid diluent, including carriers, such as talc, zeolites, Alder bark, kaolin, diatomaceous earth, mineral oil, water, and the like.

The following examples are provided to illustrate the present invention.

EXAMPLES

Example 1

(A) A potato dust inert system (PDIS) was prepared by blending the following three inert diluents in a ribbon blender: talc (Cyprus BT-200)(48.39% w/w), zeolite (16.12% w/w), and Alder bark (35.49% w/w).

The dusts listed in Table 1 below were prepared by blending PDIS and the compounds at the concentrations indicated in a ribbon blender and were evaluated for activity against *P. infestans* at the rate of application of active ingredient indicated.

TABLE 1

| Dust No. | Compound | Percent (w/w) | Percent PDIS (w/w) | Rate of Application (ppm/cwt[1]) |
|---|---|---|---|---|
| 1 | Cymoxanil | 10.5 | 89.5 | 500 |
| 2 | Cymoxanil | 5.3 | 91.5 | 250 |
| | Topsin[2] | 3.2 | | 150 |
| 3 | Dimethomorph[3] | 10.5 | 89.5 | 500 |
| 4 | Dimethomorph | 5.3 | 91.5 | 250 |
| | Topsin | 3.2 | | 150 |
| 5 | Propamocarb[4] | 10.5 | 89.5 | 500 |
| 6 | Propamocarb | 5.3 | 91.5 | 250 |
| | Topsin | 3.2 | | 150 |
| 7 | Topsin | 5.3 | 94.7 | 250 |
| 8 | Topsin | 2.6 | 89.9 | 250 |
| | Mancozeb | 7.5 | | 600 |

[1]parts per million per hundred lbs. of seed (tuber)
[2]thiophanate-methyl
[3](E,Z) 4-[3-(4-chlorophenyl)-3-(3,4-dimethoxyphenyl)acryloyl]morpholine
[4]Propyl[3-(dimethylamino)propyl]carbamate (B) The in-vitro screening procedure was conducted as follows:

Potato tubers were removed from 5° C. storage and allowed to come to room temperature. The tubers were then washed with tap water and sterilized in 5% commercial bleach (Clorox) for 10 minutes. The tubers were then rinsed in sterile distilled water and dried.

*Phytophthora infestans* was grown on agar plates at 18° C. for 10–14 days. 20 ml. of 5° C. sterile distilled water were then added to each plate. The agar was then agitated or cut into smaller sections and placed at 10–12° C. for 2 hours to release zoospores.

Tubers were cut into uniform sized slices (1 cm thick). Each dust was applied to 20 slices at 0.5 lb/cwt. Two sets of 20 potato slices were left untreated with dust and used as controls. Each dusted potato slice was then placed on sterile moistened filter paper in a sterile petri dish.

A zoospore suspension was quantified to a concentration of 20,000 spores/ml. 100 ul of this spore suspension was then applied to a sterile filter paper disk. One such treated disk was placed in the center of each potato slice. One set of 20 undusted potato slices were not inoculated and used as a sterile control.

Each potato slice was then placed in the dark at 18° C. for 7 days. After the 7 days, the disease state of each potato slice was assessed.

In Table 2 below, growth and sporulation of *P. infestans* for each potato slice was rated on a plus (+) or minus (−) scale. A minus indicates no growth of the *P. infestans* whereas a plus indicates growth. Growth was measured as minimal (+), good (++), or good and sporulation (+++).

TABLE 2

GROWTH AND SPORULATION OF *P. INFESTANS*

| Dust No. | Growth |
|---|---|
| 1 | − |
| 2 | − |
| 3 | − |
| 4 | − |
| 5 | +++ |
| 6 | ++ |
| 7 | + |
| 8 | − |
| Untreated | +++ |
| Sterile | − |

Example 2

(A) Dusts were prepared as described in Example 1 above.

(B) The in-vivo screening procedure was conducted as follows:

Potato tubers were removed from 5° C. storage and allowed to come to room temperature. The tubers were then washed with tap water and sterilized in 5% commercial bleach (Clorox) for 10 minutes. The tubers were then rinsed in sterile distilled water and dried.

*Phytophthora infestans* was grown on agar plates at 18° C. for 10–14 days. 20 ml. of 50° C. sterile distilled water were then added to each plate. The agar was then agitated or cut into smaller sections and placed at 10–12° C. for 2 hours to release zoospores. A zoospore suspension was quantified to a concentration of 20,000 spores/ml.

Small punctures were made in the tubers with a sterile needle and the punctured tubers were then dipped into the suspension of *P. infestans* zoospores. The tubers were then incubated at 15° C. with 95% relative humidity for 7–10 days. After the incubation the tubers were then cut into 2–4 oz. pieces. Each dust was applied to 15 pieces at 0.5 lb/cwt or according to manufacturer's directions. One set of 15 pieces was left untreated and used as a control.

Potatoes not dipped in the zoospores were also cut into 2–4 oz. pieces and one set of 15 uninaoculated potato pieces was used as a sterile control.

The potato pieces were then placed in sandy soil and incubated at 17° C. days and 13° C. nights for 32 days. Growth after emergence was monitored for 14–28 days. Disease symptoms were visually rated. Stem/leaf tissue was assayed for *P. infestans* on appropriate media. Finally, potato seed pieces were then removed and cut in half and disease presence was visually assessed.

The results of this test are presented below in Tables 3 and 4.

TABLE 3

Germination and Emergence Results

| Dust No. | Emergence (%) Day 14 | Germination (%) Day 32 |
|---|---|---|
| 1 | 33.3 | 100 |
| 2 | 33.3 | 100 |
| 3 | 26.7 | 80 |
| 4 | 33.3 | 53.3 |
| 6 | 20 | 40 |
| 8 | 6.7 | 6.7 |
| Untreated | 20 | 13.3 |
| Sterile | 33.3 | 100 |

TABLE 4

TUBER AND STEM HEALTH

| Dust No. | A[1] (%) | B[2] (%) | C[3] (%) | D[4] (%) |
|---|---|---|---|---|
| 1 | 0 | 0 | 26.7 | 73.3 |
| 2 | 0 | 0 | 0 | 100 |
| 3 | 20 | 26.7 | 53.3 | 0 |
| 4 | 40 | 13.3 | 40 | 0 |
| 6 | 60 | 20 | 20 | 0 |
| 8 | 93.3 | 6.7 | 0 | 0 |
| Untreated | 86.7 | 13.3 | 0 | 0 |
| Sterile | 0 | 0 | 0 | 100 |

[1]Blighted tuber; No emergence
[2]Blighted tuber; Small-sized infected stems
[3]Blighted tuber; Average-sized infected stems
[4]Clean tubers; Healthy uninfected stems Example 3

The following new dusts in Table 5 were prepared as described in Example 1.

TABLE 5

| Dust No. | Compound | Percent (w/w) | Percent PDIS (w/w) | Rate of Application (ppm/cwt) |
|---|---|---|---|---|
| 9 | Cymoxanil | 5.3 | 94.7 | 250 |
| 10 | Cymoxanil | 2.1 | 94.7 | 100 |
| | Topsin[2] | 3.2 | | 150 |
| 11 | Cymoxanil | 4.2 | 92.6 | 200 |
| | Topsin | 3.2 | | 150 |
| 12 | Cymoxanil | 2.1 | 92.2 | 100 |
| | Mancozeb | 2.5 | | 100 |
| | Topsin | 3.2 | | 150 |
| 13 | Topsin | 5.2 | 87.3 | 500 |
| | Mancozeb | 7.5 | | 600 |

These dusts were tested using the procedure described in Example 2 above. The results of this testing is shown in Table 6 below.

TABLE 6

EMERGENCE AND TUBER AND STEM HEALTH

| | Emergence (%) | | | Infection (%) | |
|---|---|---|---|---|---|
| Dust No. | Day 15 | Day 23 | Day 35 | Tubers | Stems |
| 9 | 0 | 20 | 80 | 20 | 0 |
| 10 | 0 | 0 | 60 | 40 | 33.3 |
| 11 | 0 | 20 | 100 | 40 | 33.3 |
| 12 | 20 | 80 | 100 | 0 | 0 |

TABLE 6-continued

EMERGENCE AND TUBER AND STEM HEALTH

| | Emergence (%) | | | Infection (%) | |
|---|---|---|---|---|---|
| Dust No. | Day 15 | Day 23 | Day 35 | Tubers | Stems |
| 13 | 0 | 0 | 0 | 100 | no stems |
| Untreated | 0 | 0 | 0 | 100 | no stems |
| Sterile | 0 | 100 | 100 | 0 | 0 |

Example 4

The following dusts in Table 7 were prepared as described in Example 1.

TABLE 7

| Dust No. | Compound | Percent (w/w) | Percent PDIS (w/w) | Rate of Application (ppm/cwt) |
|---|---|---|---|---|
| 14 | Mancozeb (80%) | 10.0 | 90.0 | 400 |
| 15 | Cymoxanil (96%) | 2.1 | 97.9 | 100 |
| 16 | Cymoxanil (96%) | 2.1 | 90.9 | 100 |
| | Mancozeb (80%) | 7.5 | | 300 |
| 17 | Topsin (95%) | 3.2 | 92.8 | 150 |
| | Cymoxanil (50%) | 4.0 | | 100 |
| 18 | Topsin (95%) | 3.2 | 84.7 | 150 |
| | Mancozeb (80%) | 10.0 | | 400 |
| | Cymoxanil (96%) | 2.1 | | 100 |
| 19 | Topsin (95%) | 3.2 | 87.3 | 150 |
| | Mancozeb (80%) | 7.5 | | 300 |
| | Cymoxanil (96%) | 2.1 | | 100 |

These dusts (as well as Dust Nos. 7 and 8) were tested using the procedure described in Example 2 above using Russet Burbank tubers. The results of this testing (10 replications/treatment) are shown in Table 8 below.

TABLE 8

EMERGENCE AND STEM HEALTH

| | Emergence (%) | | Infection (%) |
|---|---|---|---|
| Dust No. | Day 14 | Day 28 | Stems |
| 7 | 0 | 0 | no stems |
| 8 | 10 | 10 | 100 |
| 14 | 0 | 10 | 100 |
| 15 | 30 | 40 | 25 |
| 16 | 20 | 40 | 0 |
| 17 | 10 | 30 | 33 |
| 18 | 30 | 40 | 0 |
| Untreated | 0 | 0 | no stems |
| Sterile | 60 | 100 | 0 |

Example 5

The dusts prepared in Example 4 above (as well as Dust Nos. 7 and 8) were tested using the procedure described in Example 2 above using Red Nordland tubers. The results of this testing (7 replications/treatment) are shown in Table 9 below.

TABLE 9

EMERGENCE AND STEM HEALTH

| | Emergence (%) | | Infection (%) |
|---|---|---|---|
| Dust No. | Day 10 | Day 38 | Stems |
| 7 | 0 | 0 | no stems |
| 8 | 14.3 | 14.3 | 100 |
| 14 | 0 | 0 | no stems |
| 15 | 85.7 | 100 | 14 |
| 16 | 57.1 | 85.7 | 0 |
| 17 | 42.9 | 85.7 | 14 |
| 18 | 71.4 | 100 | 0 |
| Untreated | 0 | 0 | no stems |
| Sterile | 57.1 | 100 | 0 |

Example 6

Shepody potato tubers were contaminated/inoculated with *Phytophthora infestans* and set aside ("source tubers"). After two weeks, one (1) source tuber was cut into quarters through the diseased area with a cutting knife. Without cleaning or changing the knife, five (5) uninoculated Shepody potato tubers were then cut into quarters. This process (1 source tuber/5 uninfected tubers) was repeated to provide enough tubers for 30 replications per treatment (Table 10 below).

The cut tubers (source and uninoculated) were weighed and the appropriate amount of each dust listed in Table 10 below was applied to the tubers by placing the tubers in a double paper bag with dust and then shaking the bag.

The treated tubers were then placed in an unsealed plastic bag (one bag per treatment) and incubated at 10° C., 80–90% RH, for two (2) weeks. After two (2) weeks, the bagged tubers were removed from the 10° C., 80–90% RH environment. The bags were then rolled or shaken to simulate movement from storage to planting areas. The tubers were removed and the spread of *P. infestans* was determined—% infected tubers. The tubers were warmed to room temperature and planted. The source tubers were not planted. Emergence and infection data were obtained as described above in Example 2 (30 replications/treatment).

The results of this test are listed below in Table 10.

TABLE 10

EMERGENCE AND TUBER AND STEM HEALTH

| | Emergence (%) | | Infection (%) | |
|---|---|---|---|---|
| Dust No. | Day 6 | Day 20 | Tubers (Before planting) | Stems |
| 7 | 20 | 86.7 | 60 | 40 |
| 8 | 26.7 | 80 | 40 | 20 |
| 14 | 20 | 83.3 | 20 | 10 |
| 15 | 30 | 100 | 20 | 0 |
| 17 | 40 | 93.3 | 40 | 0 |
| 18 | 56.7 | 100 | 30 | 0 |
| 19 | 20 | 100 | 30 | 0 |
| Untreated | 16.7 | 70 | 90 | 40 |

Example 7

The procedure described above in Example 6 was repeated using Red Nordland potato tubers. The results of this test are present below in Table 11.

TABLE 11

EMERGENCE AND TUBER AND STEM HEALTH

| Dust No. | Emergence (%) Day 8 | Emergence (%) Day 25 | Infection (%) Tubers (Before planting) | Infection (%) Stems |
|---|---|---|---|---|
| 7 | 20 | 83.3 | 47.5 | 33 |
| 8 | 20 | 83.3 | 52.5 | 33 |
| 14 | 30 | 70 | 52.5 | 0 |
| 15 | 26.7 | 90 | 50 | 0 |
| 17 | 26.7 | 96.7 | 45 | 0 |
| 18 | 36.7 | 100 | 45 | 0 |
| 19 | 20 | 96.7 | 35 | 0 |
| Untreated | 10 | 20 | 60 | 33 |
| Sterile | 36.7 | 100 | 0 | 0 |

The results in Tables 10 and 11 demonstrate that tubers contaminated with *P. infestans* spread from a contaminated seed source through the cutting and handling of the tubers prior to treatment and planting, still produced plants that were disease free when the tubers were treated in accordance with the present invention prior to planting.

What is claimed is:

1. A method for combating plant fungi in a plant which comprises applying to the seeds or tubers of the plant to form treated seeds or tubers, an effective amount of composition comprising an enhanced fungicidally effective amounts of:

a) a 2-alkoxyiminoacetamide compound of the formula:

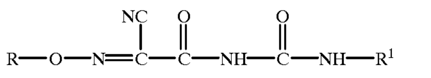

wherein R is methyl or ethyl and $R^1$ is hydrogen, $C_1$–$C_4$ alkyl or allyl;

b) an alkylene bis-dithiocarbamate complex salt of the formula:

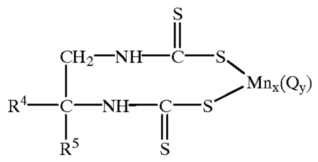

wherein $R^4$ and $R^5$ are each, independently, hydrogen or $C_1$–$C_6$ alkyl; Q is Zn, Fe, or Cu; and the ratio of x to y is from about 3:1 to about 100:1; and c) a thiophanate compound of the formula:

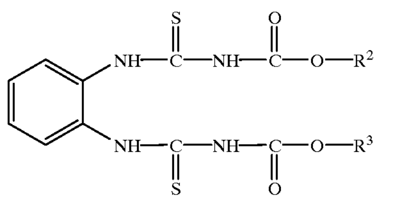

wherein $R^2$ and $R^3$ are each, independently, $C_1$–$C_6$ alkyl, wherein said fungicidal composition is applied at a rate of from about 50 or more ppm per 100 pounds of seed or tuber.

2. A method as in claim 1 wherein said fungicidal composition includes a carrier.

3. A method as recited in claim 1 wherein $R^1$ and $R^2$ and $R^3$ are each, independently, $C_1$–$C_4$ alkyl, and $R^4$ and $R^5$ are each, independently, hydrogen or $C_1$–$C_4$ alkyl.

4. A method as recited in claim 3 wherein $R^1$, $R^2$, and $R^3$ are each, independently, methyl or ethyl, and $R^4$ and $R^5$ are each, independently, hydrogen, methyl or ethyl.

5. A method as recited in claim 4 wherein Q is Zn and the ratio of x to y is from about 5:1 to about 20:1.

6. A method as recited in claim 5 wherein the ratio of x to y is from about 6:1 to about 10:1.

7. A method as recited in claim 6 wherein said 2-alkoxyiminoacetamide compound is cymoxanil; said alkylene bis-dithiocarbamate complex salt compound is mancozeb; and said thiophanate compound is thiophanate-methyl.

8. A method as recited in claim 1 wherein the plant is a potato plant.

9. A method as recited in claim 8 wherein the fungi is the Late Blight fungus, *Phytophthora infestans*.

10. A method as in claim 1 wherein said fungicidal composition is applied at a rate of from 300 ppm to about 900 ppm per 100 pounds of seed or tuber.

11. A method as in claim 1 wherein said fungicidal composition is applied at a rate of from 300 ppm to about 700 ppm per 100 pounds of seed or tuber.

12. A method as in claim 7 wherein said fungicidal composition is applied at a rate of from 300 ppm to about 1200 ppm per 100 pounds of seed or tuber.

13. A method for combating plant fungi in a plant which comprises applying to the seeds or tubers of the plant, an effective amount of a fungicidal composition comprising an enhanced fungicidally effective amounts of:

a) a 2-alkoxyiminoacetamide compound of the formula:

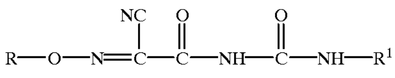

wherein R is methyl or ethyl and $R^1$ is hydrogen, $C_1$–$C_4$ alkyl or allyl;

b) an alkylene bis-dithiocarbamate complex salt of the formula:

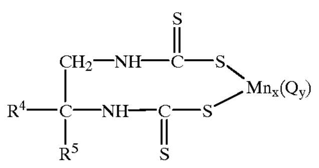

wherein $R^4$ and $R^5$ are each, independently, hydrogen or $C_1$–$C_6$ alkyl; Q is Zn, Fe, or Cu; and the ratio of x to y is from about 3:1 to about 100:1:

c) a thiophanate compound of the formula:

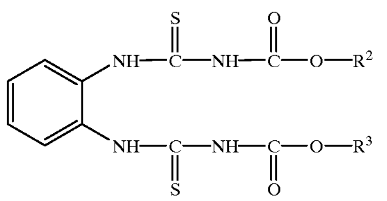

wherein $R^2$ and $R^3$ are each, independently, $C_1$–$C_6$ alkyl; and wherein said 2-alkoxyiminoacetamide compound, said alkylene bis-dithiocarbamate complex salt compound and said thiophanate compound are present in a ratio of from about 3:1:1 to about 1:16:6.

14. A method as recited in claim 13 wherein the plant is a potato plant.

15. A method as recited in claim 13 wherein the fungi is the Late Blight fungus, *Phytophthora infestans*.

16. A method as recited in claim 13 wherein the 2-alkoxyiminoacetamide compound is cymoxanil; and the thiophanate compound is thiophanate-methyl.

17. A method as in claim 13 wherein said fungicidal composition includes a carrier.

18. A method as in claim 13 wherein said fungicidal composition is applied at a rate of from 50 ppm to about 1200 ppm per 100 pounds of seed or tuber.

19. A method as in claim 13 wherein said fungicidal composition is applied at a rate of from 300 ppm to about 900 ppm per 100 pounds of seed or tuber.

20. A method as in claim 13 wherein said fungicidal composition is applied at a rate of from 300 ppm to about 700 ppm per 100 pounds of seed or tuber.

21. A method as recited in claim 13 wherein said 2-alkoxyiminoacetamide compound is cymoxanil; said alkylene bis-dithiocarbamate complex salt compound is mancozeb; and said thiophanate compound is thiophanate-methyl.

22. A method as in claim 21 wherein said fungicidal composition is applied at a rate of from 300 ppm to about 1200 ppm per 100 pounds of seed or tuber.

* * * * *

UNITED STATES PATENT AND TRADEMARK OFFICE

CERTIFICATE OF CORRECTION

PATENT NO. : 6,228,883 B1
DATED : May 8, 2001
INVENTOR(S) : Jennifer Lynn Riggs

It is certified that error appears in the above-identified patent and that said Letters Patent is hereby corrected as shown below:

Column 9, claim 1,
Line 28, after "amount of", insert -- a fungicidal --.

Signed and Sealed this

Fifth Day of March, 2002

*Attest:*

JAMES E. ROGAN

*Attesting Officer*

*Director of the United States Patent and Trademark Office*